(12) United States Patent
Monroe et al.

(10) Patent No.: US 9,044,584 B2
(45) Date of Patent: Jun. 2, 2015

(54) PNEUMATIC CONNECTOR FOR SMALL-BORE MEDICAL TUBING

(75) Inventors: Charles C. Monroe, Hudson, MA (US); Joseph A. Coviello, Derry, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 392 days.

(21) Appl. No.: 13/143,251

(22) PCT Filed: Dec. 15, 2009

(86) PCT No.: PCT/IB2009/055769
§ 371 (c)(1),
(2), (4) Date: Jul. 5, 2011

(87) PCT Pub. No.: WO2010/079396
PCT Pub. Date: Jul. 15, 2010

(65) Prior Publication Data
US 2011/0266796 A1 Nov. 3, 2011

Related U.S. Application Data

(60) Provisional application No. 61/142,669, filed on Jan. 6, 2009.

(51) Int. Cl.
| F16L 37/00 | (2006.01) |
| A61M 39/10 | (2006.01) |
| A61B 5/022 | (2006.01) |
| F16L 37/24 | (2006.01) |
| F16L 37/248 | (2006.01) |

(52) U.S. Cl.
CPC ............. *A61M 39/10* (2013.01); *A61B 5/022* (2013.01); *A61B 2562/225* (2013.01); *A61M 39/1011* (2013.01); *A61M 2039/1027* (2013.01); *A61M 2039/1094* (2013.01); *A61M 2205/582* (2013.01); *F16L 37/24* (2013.01); *F16L 37/248* (2013.01)

(58) Field of Classification Search
USPC ................. 285/376, 401, 320, 305, 239, 242
See application file for complete search history.

(56) References Cited

U.S. PATENT DOCUMENTS

| 778,936 | A | * | 1/1905 | Witmond | 285/239 |
| 894,900 | A | * | 8/1908 | Pohlman | 285/415 |
| 943,900 | A | * | 12/1909 | Smith | 285/376 |
| 1,128,474 | A | * | 2/1915 | Martz | 285/376 |

(Continued)

FOREIGN PATENT DOCUMENTS

| CA | 2100854 A1 | 1/1994 |
| CN | 1311704 A | 9/2001 |

(Continued)

*Primary Examiner* — David E Bochna

(57) ABSTRACT

A connector apparatus for small-bore medical tubing includes a male connector (20) with a dome (22) which fits into a mating cavity (42) of a female connector (40) when the two connectors are coupled together. A fluid channel extends through the connectors, the dome, and into the cavity to form a continuous fluid passageway when the connectors are coupled together. The dome is compressed into the cavity to form a fluid-tight connection when the connectors are coupled together. Each connector has a coupling structure which mates with the other to compress the connectors together when fully engaged. The connectors are engaged by inserting the dome of one of the connectors into the cavity of the other connector, then rotating the connectors to fully couple them together.

9 Claims, 4 Drawing Sheets

(56) References Cited

U.S. PATENT DOCUMENTS

| | | | |
|---|---|---|---|
| 1,194,793 A * | 8/1916 | Styers | 285/376 |
| 1,274,406 A * | 8/1918 | Frazier et al. | 285/376 |
| 1,994,784 A * | 3/1935 | Porzel | 285/239 |
| 2,190,220 A | 2/1940 | Schilling | |
| 4,068,870 A * | 1/1978 | Whitney et al. | 285/320 |
| 4,428,560 A * | 1/1984 | Erdelsky | 285/376 |
| 4,502,701 A * | 3/1985 | Treloar et al. | 285/352 |
| 4,632,433 A * | 12/1986 | Kimura | 285/376 |
| 5,005,875 A * | 4/1991 | Harle | 285/239 |
| 5,330,235 A * | 7/1994 | Wagner et al. | 285/320 |
| 5,397,196 A * | 3/1995 | Boiret et al. | 285/401 |
| 5,645,539 A | 7/1997 | Solomon et al. | |
| 5,681,063 A * | 10/1997 | Bressner | 285/376 |
| 5,775,744 A * | 7/1998 | Smith, III | 285/401 |
| 6,126,610 A | 10/2000 | Rich et al. | |
| 6,152,495 A * | 11/2000 | Hoffmann et al. | 285/239 |
| 6,302,445 B1 * | 10/2001 | Kugele et al. | 285/376 |
| 6,505,866 B1 * | 1/2003 | Nakamura et al. | 285/239 |
| 6,702,337 B2 * | 3/2004 | Rutter et al. | 285/401 |
| 7,137,654 B2 | 11/2006 | Segal et al. | |
| 7,681,925 B2 * | 3/2010 | Lambert et al. | 285/376 |
| 7,878,553 B2 * | 2/2011 | Wicks et al. | 285/305 |
| 8,322,756 B2 * | 12/2012 | Elton et al. | 285/376 |
| 8,578,979 B2 * | 11/2013 | Johnson | 141/372 |
| 2002/0089181 A1 * | 7/2002 | Sampson | 285/376 |
| 2004/0164550 A1 * | 8/2004 | Knowles et al. | 285/239 |
| 2005/0082828 A1 * | 4/2005 | Wicks et al. | 285/320 |
| 2006/0103133 A1 * | 5/2006 | Moretti et al. | 285/305 |
| 2008/0139950 A1 | 6/2008 | Molnr et al. | |
| 2012/0074146 A1 * | 3/2012 | Kunishige et al. | 285/305 |
| 2013/0320672 A1 * | 12/2013 | Steele | 285/305 |

FOREIGN PATENT DOCUMENTS

| | | |
|---|---|---|
| JP | 57140990 A | 8/1982 |
| JP | 61171903 A | 8/1986 |
| JP | 2008532652 A | 8/2008 |
| JP | 03145253 U | 10/2008 |
| WO | 9221163 A1 | 11/1992 |
| WO | 9414045 A1 | 6/1994 |
| WO | 9614894 A1 | 5/1996 |
| WO | 0298046 A2 | 5/2002 |

* cited by examiner

PNEUMATIC CONNECTOR FOR SMALL-BORE MEDICAL TUBING

This invention relates to fluid connections for medical devices and, in particular, to pneumatic connectors for small-bore tubing that conducts a fluid such as a liquid or a gas.

Numerous medical devices use pneumatic tubing to conduct fluids such as liquids or gases to or from a patient. A saline bag may be connected to an IV needle to administer pharmaceutical compounds to a patient, for example. Tubing may be needed to connect a patient mask to an instrument which measures the patient's respiratory gases or supplies oxygen to the patient. Another instance which requires pneumatic tubing is a non-invasive blood pressure monitor. For periodic monitoring at the bedside, an inflatable pressure cuff is wrapped around the arm of the patient. The pressure cuff is coupled by pneumatic tubing to a non-invasive blood pressure monitor. Periodically the blood pressure monitor will inflate the cuff around the arm of the patient, then slowly allow the pressure of the cuff to be released as the systolic and diastolic pressure levels are measured. Blood pressure cuffs come in a variety of different sizes. When a different size cuff is needed, the current cuff and its tubing are disconnected from a length of tubing attached to the blood pressure monitor and the tubing of a different cuff is connected to the monitor's tubing. Generally a longer section of tubing extends from the blood pressure monitor and terminates at connector which mates with the connector on the tubing of the blood pressure cuff. When the connectors are coupled together, the two tubing sections are joined in a fluid-tight connection that will not leak under the pressure of cuff inflation. In some cases the blood pressure cuff and its length of tubing are only used with a single patient. When the patient's blood pressure is no longer being monitored the pressure cuff and its short length of tubing and connector may be discarded.

Blood pressure cuffs are divided into two general classes, neonatal and adult, each class comprising multiple sizes, from the smallest neonatal to the largest adult. The automated blood pressure monitoring industry supports numerous types of connectors for adult size cuffs. For neonatal patients the "Slip Luer" connector has gained widespread acceptance. But it is important that the connector used for neonatal cuffs be different from any connector used for adult cuffs, as the monitor hose and algorithm are different for neonatal monitoring. Safety concerns have been raised about the use of the Luer connector in blood pressure monitoring since Luer connectors are also used in IV lines, and misconnections of a non-invasive blood pressure monitor to an IV tube have been reported. Accordingly the present invention provides a different type of connector which replaces the Luer connector for use in neonatal blood pressure monitoring. Implementations of the connector of the present invention can be used in other medical and non-medical applications requiring a pneumatic connection.

In accordance with the principles of the present invention, a pneumatic connector is described which utilizes a dome and cavity connection as the pneumatic interface. Mating male and female connectors with this pneumatic interface may be coupled together and released by a simple quarter-turn. Each connector has a mating coupling mechanism which holds the coupled connectors together when engaged. A detent mechanism which provides a tactile sensation when the connector is engaged may also be used. The dome and cavity connection obviates the need for an O-ring seal commonly required by standard pneumatic connectors.

Figure 1:
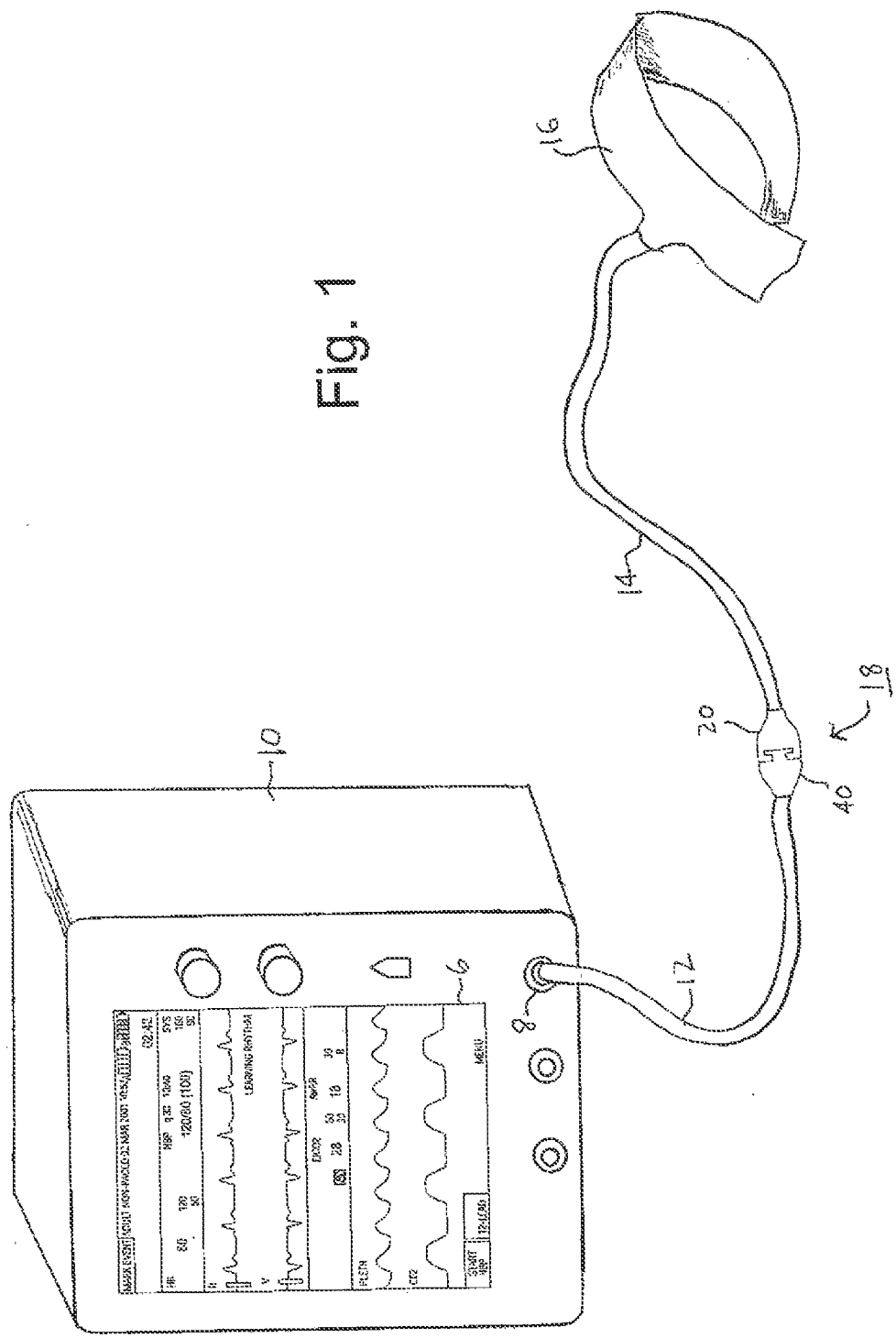
FIG. 1 illustrates the pneumatic tubing of a monitoring instrument coupled to a blood pressure cuff by a pneumatic connector of the present invention.

Referring first to FIG. 1, a monitoring instrument 10 is shown connected by pneumatic tubing sections 12 and 14 to a blood pressure cuff 16. The inflatable cuff 16 is generally wrapped around the upper arm of a patient and held securely with overlapping hook-and-loop fasteners. A relatively short section 14 of small-bore flexible tubing is fastened to the cuff 16 and provides air to inflate a bladder within the cuff. The tubing section 14 terminates at a pneumatic connector 20. Another, generally longer, section of tubing 12 is coupled at one end to an inflation port 8 of the monitoring instrument 10. The tubing section 12 terminates at a pneumatic connector 40. The monitoring instrument shown in this example is one which monitors a number of bodily functions such as the patient's ECG, heart rate, and $CO_2$, among other functions. The patient's recent blood pressure measurement is shown on the second line of the display 6 of the monitor, which is 120/80 in this example. In typical use, the monitoring instrument is set to take a measurement periodically at predetermined intervals. At each interval the monitoring instrument will inflate, the cuff 16 through the tubing sections 12,14 until the blood vessels in the upper arm are occluded. The inflation pressure is then gradually bled off until normal blood flow returns, and, using the oscillometric method, the monitoring instrument calculates the systolic and diastolic blood pressure levels from mean and other arterial pressure measurements taken over the inflation cycle. The measurements are recorded and stored by the monitoring instrument and the most recent reading is displayed on the monitor display 6.

Figure 2:
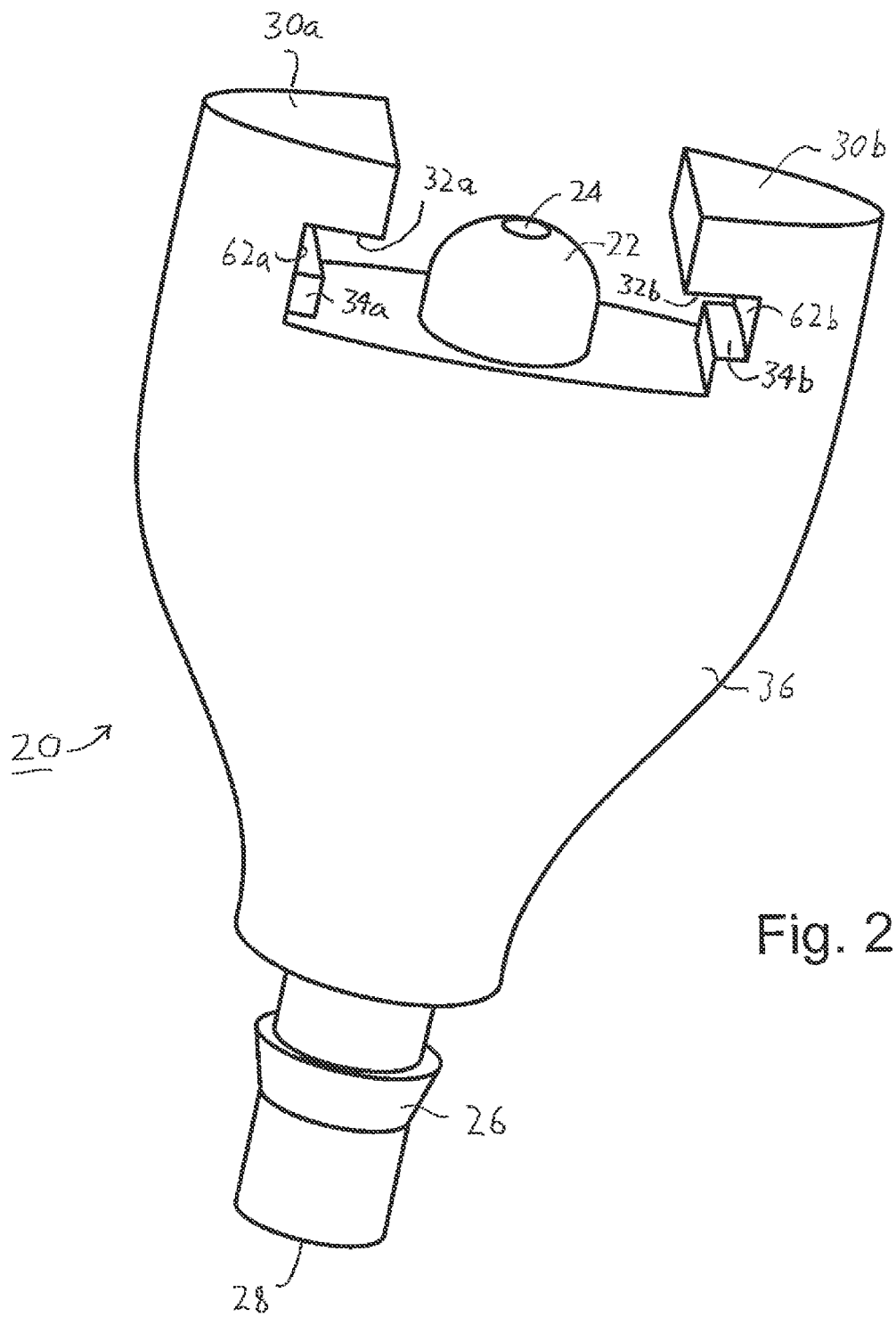
FIG. 2 is an enlarged view of the male connector of a pneumatic connector of the present invention.

In accordance with the principles of the present invention the sections of tubing 12, 14 are pneumatically coupled by a connector 18 which includes the two mating connectors 20 and 40. The male connector 20, which is located at the end of the cuff tubing section 14 in this example, is shown in the enlarged view of FIG. 2. The male connector 20 includes a dome 22 with a fluid aperture 24 extending as a channel through the dome, through the body 36 of the connector, through a hose barb 26 to the proximal end 23 of the connector. It is the purpose of the dome 22 to form a fluid-tight connection of the fluid aperture 24 when the male and female connectors are connected together as shown in FIG. 1. The body 36 of the male connector is not symmetrical (is asymmetric) in four directions, that is, it is not square or circular for the reasons described below. The hose barb 26 will provide a fluid-tight connection to the hose or small bore tubing which is slipped over the barb to connect the connector to tubing. The male connector 20 has two arms 30a and 30b which will align with shoulders on the female connectors when the two connectors are coupled together. The distal surfaces 32a and 32b of the undercuts of the arms 30a and 30b are slightly tapered in the axial direction of the connector so that the mating arms and shoulders will pull the male and female connectors tightly together and compress the dome 22 in a fluid-tight fit when the two connectors are coupled together. The outer proximal surfaces of the undercuts contain ribs 34a and 34b which travel in mating channels in the female connector as the two connectors are coupled together. To prevent over-rotation when connecting the male and female connectors together, the ribs 34a and 34b of the male connector encounter stops in the female connector when the male and female connectors are fully engaged and coupled together.

Figure 3:
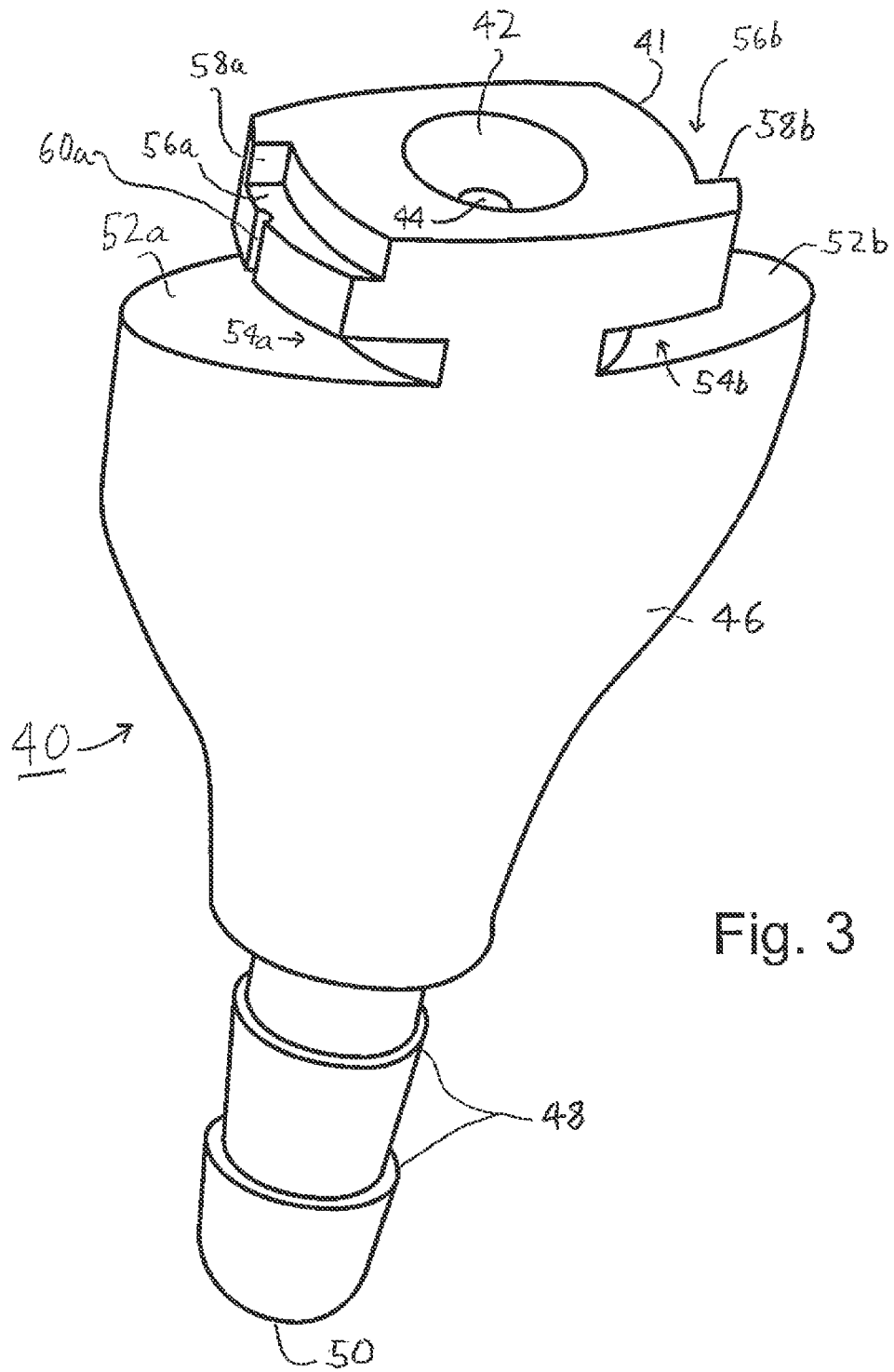
FIG. 3 is an enlarged view of the female connector of a pneumatic connector of the present invention.

The female connector 40 is shown in an enlarged view in FIG. 3. At the proximal end (top) of the female connector 40 is a cavity extension 41 with a cavity 42 which is sized and shaped to mate with the dome 22 of the male connector. In a constructed embodiment the cavity 42 is slightly smaller than the dome 22 so that the dome is slightly compressed in the cavity when the male and female connectors are coupled together, thereby providing a good fluid-tight fit. At the bottom of the cavity 44 is a fluid aperture 44 which is in line with the fluid aperture 24 of the male connector when the male and female connectors are coupled together. The fluid aperture 44 extends as a channel through the body 46 of the female connector 40, through the hose barb 48 at the proximal end of the female connector, and to the proximal end 50 of the female connector. The body of the female connector has a similar cross-axial shape as the male connector, which is generally oval in this example. The female connector 40 has shoulders 52a and 52b which align with the distal arms 30a and 30b of the male connector when the two are coupled together. When engaged, the arms 30a and 30b of the male connector 20 fit into undercuts 54a and 54b of the female connector. The undercuts 54a and 54b of the female connector are similarly slightly tapered to pull the male and female connectors tightly together when joined. Above the undercuts 54a and 54b are channels 56a and 56b (not visible in FIG. 3) in which the ribs 34a and 34b of the male connector travel as the two connectors are joined together. The ribs 34a and 34b of the male connector encounter stops 58a and 58b at the ends of the channels when the male and female connectors are fully engaged.

In this example the male and female connectors also have an optional detent mechanism which provides a tactile sensation as the male and female connectors become fully engaged. In this example the female connector 40 has a small groove or depression 60a extending axially between the undercut 54a and the channel 56a. A similar groove 60b (not visible in FIG. 3) is present on the other side of the female connector between undercut 54b and channel 56b. As the two connectors come into full engagement, the grooves 60a and 60b engage small projections extending from the walls of the undercuts of the arms 30a and 30b just above the ribs 34a and 34b. As the male and female connectors come into full engagement the projections snap into the grooves, producing a slight tactile sensation or clicking sound. Whether one or both of the sensation and sound are produced is controlled by the fabricator of the connectors by the characteristics of the design of the projections and grooves.

Figure 4:
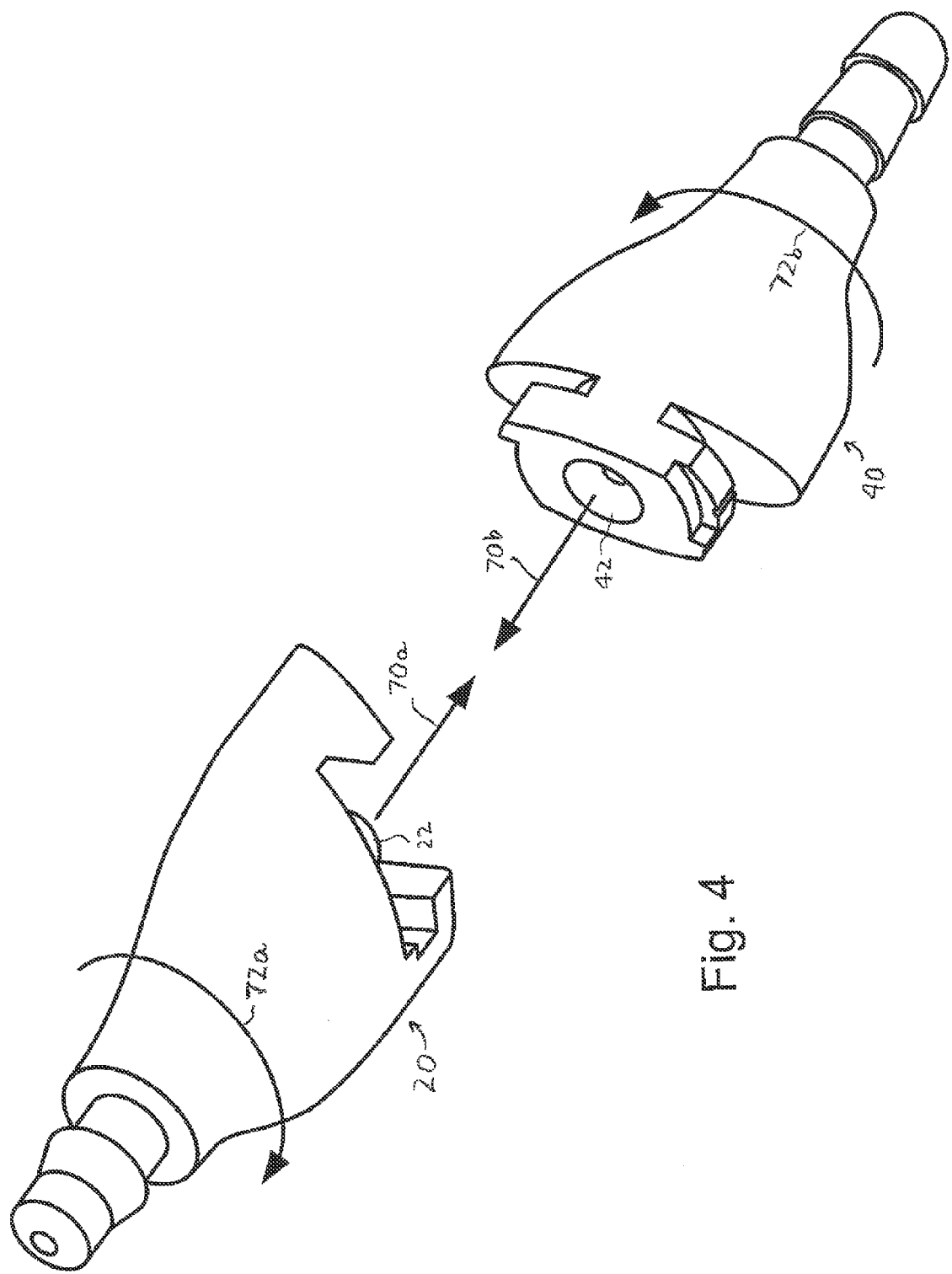
FIG. 4 illustrates the quarter-turn connecting of a pneumatic connector of the present invention.

The male and female connectors 20 and 40 are coupled together by holding them in asymmetrical opposition with the dome 22 axially aligned with the cavity 42 as shown by arrows 70a and 70b in FIG. 4. The dome 22 of the male connector 20 is inserted into the cavity 42 of the female connector 40 and the two connectors are pressed together. The two connectors are then rotated in opposite directions as indicated by the arrows 72a and 72b. The outwardly extending wings of the cavity extension 41 will then be rotated into the undercuts of the arms 30a and 30b of the male connector 20 and the arms 30a and 30b are rotated into the undercuts 54a and 54b of the female connector 40. The taper of the undercuts aids in pulling the two connectors snugly together. The ribs 34a and 34b of the male connector 20 are thereby moved into the channels 56a and 56b of the female connector 40 until the ribs contact the stops 58a and 58b of the female connector. At this point the detent mechanism 60,62, if present, will snap together and produce its designed clicking sound or tactile sensation. The two connectors are now securely joined together with the fluid apertures 24,44 aligned and sealed by the compression of the dome 22 in the cavity 42. When coupled in this manner the asymmetrically shaped bodies 36,46 of the two connectors are now symmetrically aligned as shown in FIG. 1.

The connectors are preferably formed of a polymeric material, preferably by injection molding. In a constructed embodiment the male connector was made of nylon and the female connector was made of polysulfone, although alternate materials may be used for either or both connectors. In the constructed implementation the male connector 20 which is attached to the pressure cuff 16 is formed of a slightly softer material than the female connector 40. This material difference enables the dome 22 of the male connector to better compress when fitted into the more rigid cavity 42 of the female connector, and the arms 30a,30b to slightly compress under the compression of the taper of the undercuts of the arms 30 and the undercuts 54a,54b of the female connector. It has been found that repeated connection and disconnection of the connectors can cause wear of the small projections of the detent mechanism, which is more likely when the male connector is made of a softer material. However, in the example of FIG. 1 the pressure cuff 16, its hose line 14, and its male connector 20 are a disposable part, whereas the hose line 12 for the monitoring instrument 10 and its female connector 40 are reusable. The wear of the male connector 20 in this example is thus of little consequence as the part is disposed of after its use with the patient is discontinued. Correspondingly, wear of the female connector of the harder material is negligible, and its usable life of repeated connection and disconnection is extended by the material difference.

What is claimed is:
1. A fluid connector apparatus for tubing comprising:
a male connector having a body and a dome at a distal end of the male connector, a fluid channel extending through the dome to a proximal end of the male connector, and a first coupling structure to couple the male connector to a female connector; and
a female connector having a body and a cavity at a distal end which is sized and shaped to mate with the dome of the male connector, a fluid channel extending from the cavity to a proximal end of the female connector, and a second coupling structure to couple the female connector to the male connector, wherein the fluid channels of the male and female connectors form a continuous fluid channel when the male and female connectors are coupled together,
wherein one of the coupling structures comprises a pair of extending arms and the other of the coupling structures comprises a pair of undercuts into which the arms fit when the male and female connectors are coupled together,
wherein the male and female connectors are coupled together by inserting the dome into the cavity and axially rotating at least one connectors with respect to the other connector, and further wherein the connector bodies exhibit an asymmetrical relationship to each other when the connectors are joined but not fully rotated, and a symmetrical relationship to each other when the connectors are joined and rotated into a fully coupled condition, and
further comprising a first hose barb located at the proximal end of the male connector and a second hose barb located at the proximal end of the female connector, wherein the fluid channel of each connector extends through the hose barb.

2. The fluid connector apparatus of claim 1, further comprising a first tubing section having a first end coupled to the hose barb of the male connector and a second tubing section having a first end coupled to the hose barb of the female connector.

3. The fluid connector apparatus of claim 2,
wherein the second end of one of the tubing sections is disposed to be coupled to a blood pressure cuff and the second end of the other of the tubing sections is disposed to be coupled to a medical instrument.

4. The fluid connector apparatus of claim 3, wherein the medical instrument comprises a noninvasive blood pressure monitor.

5. The fluid connector apparatus of claim 1, further comprising a detent mechanism which produces a sound and/or tactile sensation when the male and female connectors are coupled together.

6. The fluid connector apparatus of claim 5, wherein the detent mechanism further comprises a depression located in one of the connectors and a projection located in the other of the connectors, wherein the projection is aligned to mate with the depression when the male and female connectors are coupled together.

7. A fluid connector apparatus for tubing comprising:
a male connector having a body and a dome at a distal end of the male connector, a fluid channel extending through the dome to a proximal end of the male connector, and a first coupling structure to couple the male connector to a female connector; and
a female connector having a body and a cavity at a distal end which is sized and shaped to mate with the dome of the male connector, a fluid channel extending from the cavity to a proximal end of the female connector, and a second coupling structure to couple the female connector to the male connector, wherein the fluid channels of the male and female connectors form a continuous fluid channel when the male and female connectors are coupled together,
wherein one of the coupling structures comprises a pair of extending arms and the other of the coupling structures comprises a pair of undercuts into which the arms fit when the male and female connectors are coupled together,
wherein the male and female connectors are coupled together by inserting the dome into the cavity and axially rotating at least one connectors with respect to the other connector, and further wherein the connector bodies exhibit an asymmetrical relationship to each other when the connectors are joined but not fully rotated, and a symmetrical relationship to each other when the connectors are joined and rotated into a fully coupled condition, and
wherein at least one of the arms and undercuts are tapered to provide a snug fit when the connectors are coupled together.

8. The fluid connector apparatus of claim 7, wherein the snug fit of the arms and undercuts causes a compression of the dome in the cavity when the connectors are coupled together.

9. The fluid connector apparatus of claim 7, wherein the arms and undercuts are engaged by inserting the dome into the cavity and axially rotating at least one connector with respect to the other connector.

* * * * *